US012629171B2

(12) United States Patent
Blumenkranz

(10) Patent No.: US 12,629,171 B2
(45) Date of Patent: May 19, 2026

(54) LUBRICATED MEDICAL INSTRUMENT GUIDE

(71) Applicant: Intuitive Surgical Operations, Inc., Sunnyvale, CA (US)

(72) Inventor: Stephen J. Blumenkranz, Los Altos Hills, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 719 days.

(21) Appl. No.: 17/943,872

(22) Filed: Sep. 13, 2022

(65) Prior Publication Data

US 2023/0079991 A1    Mar. 16, 2023

Related U.S. Application Data

(60) Provisional application No. 63/244,202, filed on Sep. 14, 2021.

(51) Int. Cl.
| | |
|---|---|
| *A61B 17/34* | (2006.01) |
| *A61B 34/35* | (2016.01) |
| *A61B 17/00* | (2006.01) |
| *A61B 34/30* | (2016.01) |
| *A61M 25/00* | (2006.01) |

(52) U.S. Cl.
CPC ......... *A61B 17/3423* (2013.01); *A61B 34/35* (2016.02); *A61B 2017/00845* (2013.01); *A61B 2034/303* (2016.02); *A61M 2025/0047* (2013.01)

(58) Field of Classification Search
CPC ................ A61B 17/3423; A61B 34/35; A61B 2034/303; A61B 2017/3429
See application file for complete search history.

(56) References Cited

U.S. PATENT DOCUMENTS

| | | | | | |
|---|---|---|---|---|---|
| 4,475,548 | A | * | 10/1984 | Muto | A61M 16/0463 |
| | | | | | 128/207.14 |
| 5,104,389 | A | * | 4/1992 | Deem | A61M 39/0606 |
| | | | | | 604/167.04 |
| 5,207,656 | A | * | 5/1993 | Kranys | A61M 39/0606 |
| | | | | | 604/167.04 |
| 6,808,509 | B1 | * | 10/2004 | Davey | A61M 25/0668 |
| | | | | | 604/167.04 |

(Continued)

FOREIGN PATENT DOCUMENTS

WO     WO-2018145100 A1     8/2018

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Phong Son H Dang
(74) *Attorney, Agent, or Firm* — Schwegman, Lundberg & Woessner, P.A.

(57) ABSTRACT

A medical device includes a medical instrument guide. The medical instrument guide includes a guide body. The guide body includes a foam and a bore through the foam. The foam includes a plurality of open cells that hold a biocompatible lubricant. And, the bore is sized to receive a medical instrument shaft and is defined at least in part by a surface exposing the plurality of open cells holding the biocompatible lubricant to the medical instrument shaft.

18 Claims, 7 Drawing Sheets

(56)                    References Cited

U.S. PATENT DOCUMENTS

| 8,262,568 B2 * | 9/2012 | Albrecht ............ A61B 17/0293 |
| | | 600/206 |
| 9,295,523 B2 | 3/2016 | Blumenkranz et al. |
| 12,239,317 B2 * | 3/2025 | Estera ................... A61B 17/072 |
| 12,269,180 B2 * | 4/2025 | Faraji ..................... B25J 9/1692 |
| 2010/0100043 A1 * | 4/2010 | Racenet ............. A61B 17/3423 |
| | | 604/164.01 |
| 2021/0228289 A1 * | 7/2021 | Rohr Daniel ...... A61B 1/00128 |

* cited by examiner

PROXIMAL

308

306

310

302

312

314

DISTAL

LUBRICATED MEDICAL INSTRUMENT GUIDE

CLAIM OF PRIORITY

This application is a continuation of and claims the benefit of priority under 35 U.S.C. § 119(e) to U.S. Patent Application Ser. No. 63/244,202, filed on Sep. 14, 2021, which is incorporated by reference herein in its entirety.

TECHNICAL FIELD

This document relates generally to medical devices, and more particularly to lubricated sponge seals for medical devices.

BACKGROUND

Minimally invasive therapeutic and diagnostic surgical procedures can be performed by using a teleoperated surgical system that operates with at least partial computer assistance (a "telesurgical system"). The benefits of minimally invasive surgery include less patient trauma, less blood loss, and faster recovery times when compared to traditional, open incision surgery. The use of telesurgical systems that provide telepresence allows a surgeon to operate with increased control and precision when compared to minimally invasive surgeries conducted without the benefit of a telesurgical system. Examples of telesurgical systems include the da Vinci® surgical systems and the Ion® endoluminal system, both commercialized by Intuitive Surgical, Inc. of Sunnyvale, California.

In a telesurgical system, surgery is performed by a surgeon who controls a powered instrument manipulator unit. The manipulator unit includes one or more surgical instruments that are coupled to one or more corresponding teleoperated manipulators, which articulate in one or more mechanical degrees of freedom for precise positioning and manipulation of the instruments, Minimally invasive instrument shafts may be rigid or may be flexible.

During minimally invasive surgery, an instrument typically accesses a surgical site within a patient via a small incision through the patient's body wall or via a natural orifice. In some situations in which minimally invasive surgical instruments are used, such as for surgery at or near the skin surface, an instrument's shaft may not pass through the skin surface. Regardless, in most situations a minimally invasive instrument is constrained by an instrument guide at or near the incision, orifice, or skin surface to stabilize and guide the instrument as it advances and withdraws with reference to the surgical site. In many cases, a cannula acts as an instrument guide for a minimally invasive instrument. The cannula is inserted into the incision or positioned at or near the body orifice, and a shaft of the instrument is then inserted through the cannula to access the surgical area.

In some cases, a gas is introduced to the surgical site. For example, during laparoscopic surgery an insufflation gas is often used to insufflate the surgical site to provide space for the surgeon to more effectively operate the distal end of the instrument. As another example, during a minimally invasive lung biopsy via the trachea, respiratory gasses are introduced to aid patient breathing. In these situations, a gas seal is typically employed between the instrument guide and the instrument shaft to prevent the gas from escaping through the cannula during surgery. Cannula seals that are fitted into the proximal end of cannulas, and seals fitted to the proximal end of endotracheal tubes, are examples of such seals that seal against gas leakage both when an instrument is inserted through a guide and after the instrument is removed from a guide. Such seals may act as instrument shaft guides, or they may assist with guiding instrument shafts.

In other cases, the instrument shaft may be inserted through a guide that supports and guides the shaft and instrument during insertion, retraction, and/or navigation, but the guide does not necessarily seal the insufflation gas.

Some telesurgical systems may be designed to include what is sometimes referred to as telepresence. Telepresence refers to the systems, devices, methods, etc. of the surgical system that give a remote operator the impression/perspective of operating directly on the patient—being physically present at the surgical site. One aspect of telepresence includes a system that senses tissue force on an instrument and provides a haptic or other sensation to the operator, thereby giving the operator the impression of manipulating the surgical instrument directly on the patient.

Both existing instrument guides and instrument shaft seals may cause friction that is excessive, variable (e.g., frictionally noisy), and direction-dependent (i.e., in either the instrument insertion or withdrawal directions) against an instrument shaft. Such friction can interfere with fine positioning of the instrument during insertion and withdrawal. Similarly, such friction can interfere with axial (longitudinal; along the insertion-withdrawal direction) tissue force sensing as the distal end of the instrument contacts surgical patient anatomy. In addition, friction between an instrument shaft and body tissue (e.g., between a flexible catheter shaft and the trachea or bronchial airways in the lung) may cause undesirable friction that interferes with axial instrument control and force sensing.

SUMMARY

There is a need to reduce friction between an instrument guide or seal and an instrument shaft as the instrument shaft is inserted or withdrawn through the instrument guide or seal. In addition, the solution can provide for gas sealing against the instrument shaft for surgical procedures that require this feature. Still further, additional constraints on solutions to these friction reduction and related gas seal problems include compliance with all medical device standards of disinfection or sterility, as well as economy of manufacturing to make the solutions viable for use in routine surgical procedures.

Examples according to this disclosure are directed to devices and methods that include a medical instrument shaft guide (which, in some cases, may also be a seal) through which an instrument shaft is inserted prior to entering the body of a patient and which functions to lubricate the instrument shaft to reduce insertion and/or retraction friction forces on the instrument shaft during insertion and retraction of the instrument during a surgical procedure. Example instrument shaft guides may also function to lubricate the instrument shaft against forces on the shaft (e.g., from body tissue) during navigation within the body of the patient.

For example, a medical device includes a medical instrument guide. The medical instrument guide includes a guide body. The guide body includes a foam and a bore through the foam. The foam includes a plurality of open cells that hold a biocompatible lubricant. And, the bore is sized to receive a medical instrument shaft and is defined at least in part by a surface exposing the plurality of open cells holding the biocompatible lubricant to the medical instrument shaft.

Each of these non-limiting examples can stand on its own or can be combined in various permutations or combinations with one or more of the other examples.

This Summary is intended to provide an overview of subject matter of the present patent application. It is not intended to provide an exclusive or exhaustive explanation of the invention. The detailed description is included to provide further information about various aspects of the inventive subject matter of the present patent application.

BRIEF DESCRIPTION OF THE DRAWINGS

In the drawings, which are not necessarily drawn to scale, like numerals may describe similar components in different views, Like numerals having different letter suffixes may represent different instances of similar components. The drawings illustrate generally, by way of example but not by way of limitation, various examples discussed in the present document.

FIGS. 3A and 3B are top plan and section (cut along section line A-A) elevation views depicting an example instrument guide including an open cell foam body.

DETAILED DESCRIPTION

Figure 1:
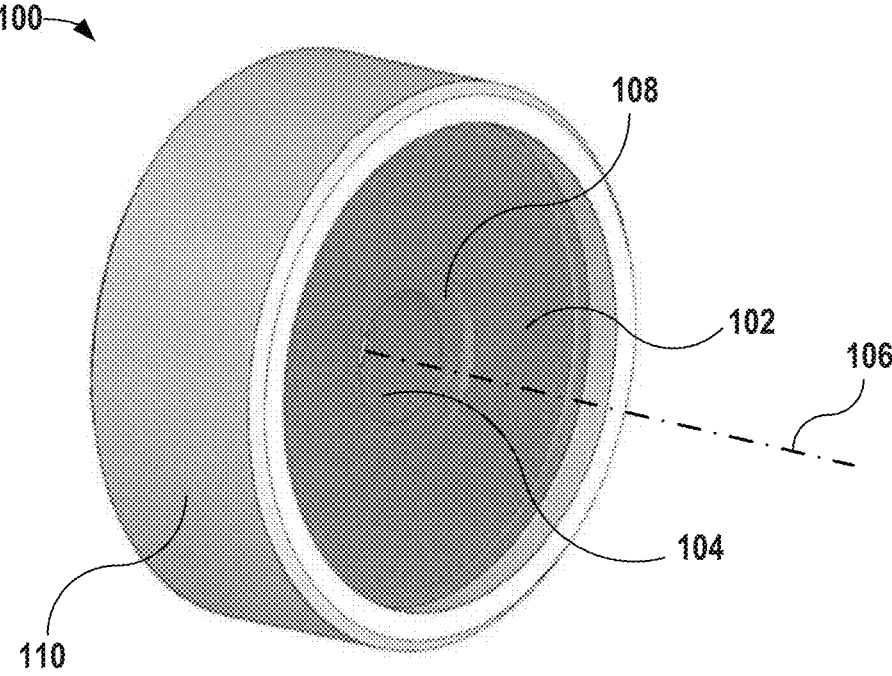
FIG. 1 is a perspective view depicting an example instrument guide in accordance with examples of this disclosure.

FIG. 1 is a perspective view depicting example instrument guide 100 in accordance with examples of this disclosure. In FIG. 1, guide 100 includes guide body 102, bore 104 (along bore axis 106), lead-in surface(s) 108, and collar 110. Guide body 102 includes bore 104 therethrough. Bore 104 is configured to receive and guide the shaft of a surgical instrument such that a longitudinal axis of the shaft is generally aligned with bore axis 106, for example during insertion and withdrawal of the instrument into and out of the body of a patient.

Guide body 102 is coupled to/mounted in collar 110. Collar 110 is just one example of a rigid or semi-rigid structure in which open guide body 102 of instrument guide 100 can be mounted and by which instrument guide 100 can be coupled to a larger surgical system, e.g., a telesurgical system. In other example instrument guides according to this disclosure, a guide body of an instrument guide may be directly coupled to a portion of the surgical system without a collar or other such structure.

Bore 104 of guide body 102 can optionally include one or more lead-in surfaces. In the example of FIG. 1, bore 104 includes lead-in surface 108, which may be a flat chamfer surface, or a rounded surface, or a combination of flat and rounded surfaces. Lead-in surface 108 may assist with the initial reception and insertion of the shaft of the instrument into and through bore 104 of guide body 102. Lead-in surface 108 may also function to limit axial distortion of guide body 102 during instrument insertion and withdrawal by reducing the contact surface between the inner surface of bore 104 and the instrument shaft. Therefore, in some embodiments a lead-in surface exists on both the insertion and withdrawal sides of guide body 102.

Guide body 102 is constructed of a sponge or open cell foam material. The open cell foam material of guide body 102 is configured to be infused/impregnated/filled with a lubricant that enables instrument guide 100 to lubricate the instrument shaft to reduce insertion and/or retraction friction forces on the instrument shaft during a surgical procedure. Instrument guide 100 and open cell foam guide body 102 may function to guide and/or seal against the shaft of the instrument. Guide body 102 is generally cylindrically shaped. In other examples according to this disclosure, however, a guide body of an instrument guide can have different 3-dimensional shapes, such as various prism (e.g., rectangular) or lenticular (e.g., single or biconvex) shapes.

Figure 2:
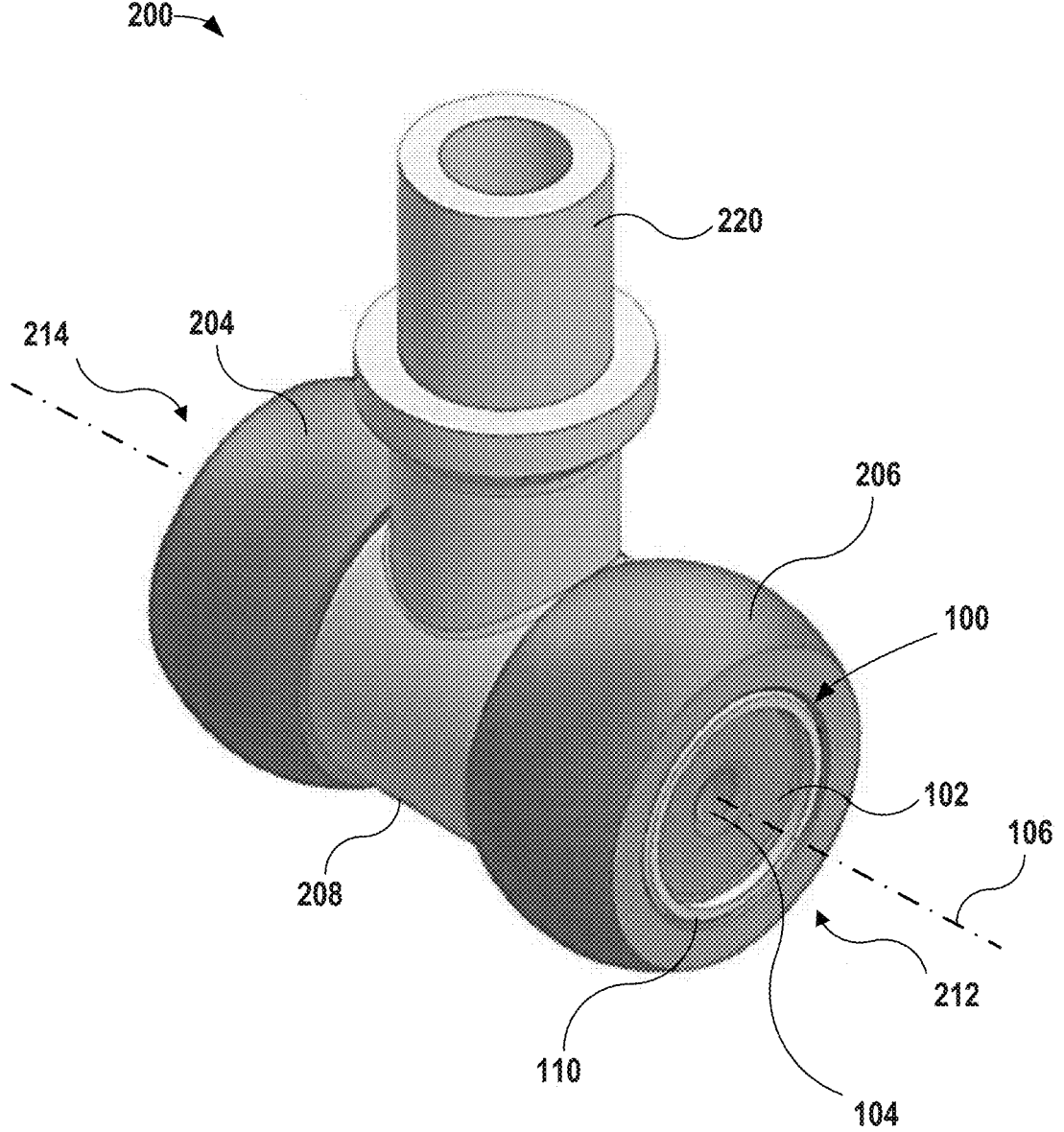
FIG. 2 is a perspective view depicting an example connection device including the example instrument guide of FIG. 1.

FIG. 2 is a perspective view depicting an example connection device 200 including the example instrument guide 100 of FIG. 1. Connection device 200 is an example of a device that may be employed to connect a telesurgical system manipulator unit to, for example, an endotracheal tube inserted into the mouth and trachea of a patient to help provide mechanical ventilation for the patient and to provide a conduit for one or more instruments included in the manipulator unit to be inserted into the lung of the patient, as will be described in more detail with reference to FIGS. 6A-6D.

Referring to FIG. 2, an example coupling device 200 is shown. Examples and details of such coupling devices are disclosed in U.S. Patent Application Pub. No. US 2021/0228289 A1 (filed Feb. 2, 2018), which is incorporated by reference. Briefly and as shown, one example connection device 200 includes two coupling members 204 and 206, one each on opposite ends of a connector body 208. As shown, coupling members 204,206 are generally toroid-shaped, and many other shapes may be used depending on mechanical coupling requirements for connection device 200. A first passage extends through the connector body 208 from a first end 212 to a second end 214 and is shaped and sized at least in part to receive instrument guide 100. An axis of the first passage is aligned with/coincident with bore axis 106 of bore 104 of guide body 102 of guide 100. Connection device 200 also includes tube 220, which is configured to couple the connection device to a source of air and/or anesthesia and join with first passage through the connector body.

Tube 220 is illustrative of various gas sources that create a pressurized gas environment on a side (typically distal) of instrument guide 100 opposite the ambient atmospheric environment on the reverse side (typically proximal) of instrument guide 100.

Second end 214 of connection device 200 may couple to an elongate device or other portion of a manipulator system of a teleoperated surgical system. And, first end 212 of connection device 200 may couple to, for example, an endotracheal tube inserted into the mouth and trachea of a patient.

Coupling members 204 and 206 are configured to mate with curved surfaces of a mounting bracket, which can be connected to, e.g., a docking spar of a manipulation unit. Coupling members 204 and 206 may be coupled to such a mounting bracket magnetically, and accordingly, members 204 and 206 and the bracket may each include magnets and/or a material responsive to a magnetic field. In some such examples, the bracket includes magnets, while coupling members 204 and 206 include magnets or a material responsive to a magnetic field, or vice-versa. Additionally, collar 110 of instrument guide 200 may be similarly magnetically coupled to coupling member 206, Although not shown in the view of FIG. 2, another example instrument guide in accordance with this disclosure could be received at and coupled to coupling member 204.

When magnetically attached, coupling members 204 and 206 may rotate about axis 106, with respect to the mounting bracket and docking spar to which the bracket is connected, while body 208 of connection device 200 remains laterally coupled to the bracket/docking spar. The amount of rotation may be limited by contact with the bracket or the bracket may permit connection device 200 to rotate a full 360°. This rotation may occur in response to slight movement of the patient or the manipulation unit.

As noted, tube 220 couples the connection device 200 to a source of air and/or anesthesia. The magnetic connection allows free rotation of connection device 200 in response to forces from the air and anesthesia tubing. With connection device 200 attached to the endotracheal tube, larger patient movement may generate a force that causes the release of the magnetically connected coupling members 204 and 206. In such cases, connection device 200 is configured to remain coupled to the endotracheal tube while being decoupled from the mounting bracket. The magnets of the members 204 and 206 may be selected to release in response to a predetermined force or motion but not release accidentally during minor motions associated with regular operation.

The toroidal shape of the connection members 204 and 206 may provide for easier installation as compared to the cylindrical shaped members and may allow release of the connection device in multiple radial directions. Other types of 360-degree magnetic surfaces may also be suitable.

Example connection device 200 may have electromagnetic connections that have a variable magnetic force at different stages of the procedure. For example, during installation, the magnetic force may be relatively low so that the user does not experience too great of a force as the connection device approaches the docking spar. During the procedure, the magnetic force may be increased. In another example, if patient movement is detected using sensors, the magnetic force may be decreased to allow for disconnect.

Additionally, a full or partial connection of connection device 200 to an associated manipulation unit may be detected using sensors. For example, if the system senses connection device 200 is disconnected, a signal can be sent to provide an error message to the operator. For this purpose, connection device 200 and/or the mounting bracket (or other structure) to which it is attached may include Hall sensors to detect when the connection device is completely seated, partially seated, or not seated to the bracket.

Connection device 200 and example instrument guide 100 in accordance with this disclosure are configured to be positioned such that the shaft of an instrument inserted into the body of a patient passes through guide 100 before entering the body. Instrument guide 100 and open cell foam guide body 102 function to guide and optionally create a gas seal against the outer surface of the shaft of the instrument. In addition, instrument guide 100 through which the instrument shaft is inserted prior to entering the body functions to lubricate the instrument shaft to reduce insertion and/or retraction friction forces on the instrument shaft during insertion and retraction of the instrument during a surgical procedure. In particular, guide body 102 is constructed of an open cell foam material configured to hold a lubricant that enables instrument guide 100 to lubricate the instrument shaft to reduce insertion and/or retraction friction forces.

In addition to lubricating the instrument shaft, instrument guide 100 and open cell foam guide body 102 may function to disinfect the shaft as it is inserted into the body. For example, open cell foam guide body 102 or portions thereof can be configured to hold a disinfectant (in addition to a lubricant) that partially or completely disinfects the instrument shaft as it is inserted in the body of the patient.

Figures 3A, 3B:
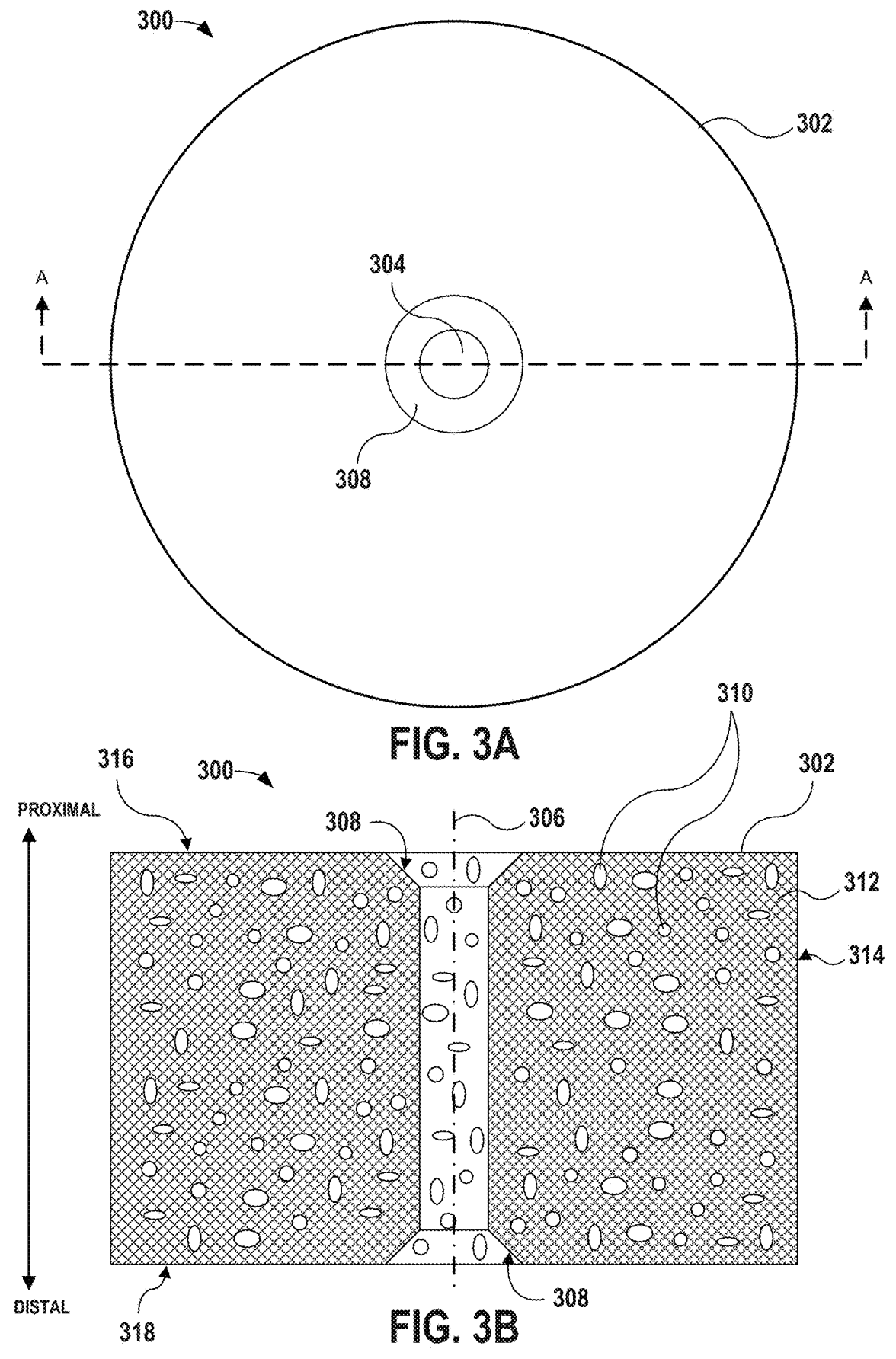

FIGS. 3A and 3B are top plan and section elevation (cut along cut line A-A) views depicting example instrument guide 300 including open cell foam body 302. Referring to FIGS. 3A and 3B, instrument guide 300 includes guide body 302, bore 304, bore-axis 306, and lead-in/lead-out surfaces 308.

Guide body 302 of guide 300 is made from an open cell foam material, which can include, for example, a variety of biocompatible open cell foam polymers. As examples, guide body 302 can include ester, ester-based, ether, and/or ether-based open cell foams, such as ester-based and ether-based polyurethane foams. (Further description is done in terms of polyurethane foams, with the understanding that such foams are illustrative of the general number of foams that may be used.) The configuration of guide body 302 is generally an open cell solid foam substrate 312 having an array of open cells 310 distributed throughout. The distribution of open cells 310 through the volume of guide body 302 can be generally even, uneven, random, etcetera. Regardless, open cells 310 of guide body 302 are configured to receive, retain for some time, and thereafter transfer one or more lubricants, and in some cases one or more disinfectants, onto a shaft of a medical instrument moving through bore 304. For example, an inner surface of bore 304 presents (includes) open cells 310 of the polymer foam to an outer surface of the instrument shaft, by which the lubricant (and/or disinfectant) is transferred from guide body 302 to the instrument shaft.

A variety of biocompatible lubricants can be held by guide body 302 (and other open cell foam guide bodies in accordance with this disclosure). For example, guide body 302 can hold a grease, oil, or water-based lubricant. In an example, guide body 302 holds a water-soluble lubricating jelly.

Guide body 302 includes outer cylindrical surface 314 and proximal and distal surfaces 316, 318 that meet the outer cylindrical surface 314. In an example, outer cylindrical surface 314, and proximal and distal surfaces 316, 318 of guide body 302 are defined by a non-porous skin that encloses open cells 310 of the polymer foam, while the surface of bore 304 does not include such a non-porous skin (or other covering). In another example, proximal and distal surfaces 316, 318 of guide body 302 are each defined by a non-porous skin that encloses open cells 310 of the polymer foam, and cylindrical surface 314 and the surface of bore 304 do not include such a non-porous skin (or other covering). In another example, open cells 310 of the polymer foam of guide body 302 are exposed on the surface of bore 304, on cylindrical surface 314, and on proximal and distal surfaces 316, 318 of guide body 302.

Guide body 302 includes optional lead-in/lead-out surfaces 308, In the example of FIGS. 3A and 3B, surfaces 308 are generally shaped as developable surfaces (i.e., a surface with zero Gaussian curvature that can be flattened into a plane without distortion—e.g., the outer surface of a conic or pyramidal frustum). In other examples, however, such instrument shaft lead-in/lead-out surfaces can be curved or contoured in a variety of shapes/profiles (e.g., a non-developable surface, such as a portion of an inner surface of a torpid, or two smooth surfaces joined at a discontinuity). In an example, proximal and distal surfaces 308 of bore 304 present open cells 310 of the polymer foam of guide body 302 to the outer surface of the instrument shaft. Stated another way, in an example, surfaces 308 of bore 304 expose open cells 310 of the polymer foam of guide body 302.

Bore 304 is configured to receive and guide the shaft of a medical instrument such that a longitudinal axis of the shaft is generally aligned with bore axis 306, for example, during insertion and withdrawal of the instrument into and out of the body of a patient. In addition to guiding, lubricating, and in some cases disinfecting the instrument shaft, guide body 302 and bore 304 may function to create a gas seal against the outer surface of the shaft. In some examples, therefore, a diameter of bore 304 is less than an outer diameter of an instrument shaft inserted through the bore to assist with sealing the outer surface of the shaft.

Figure 4:
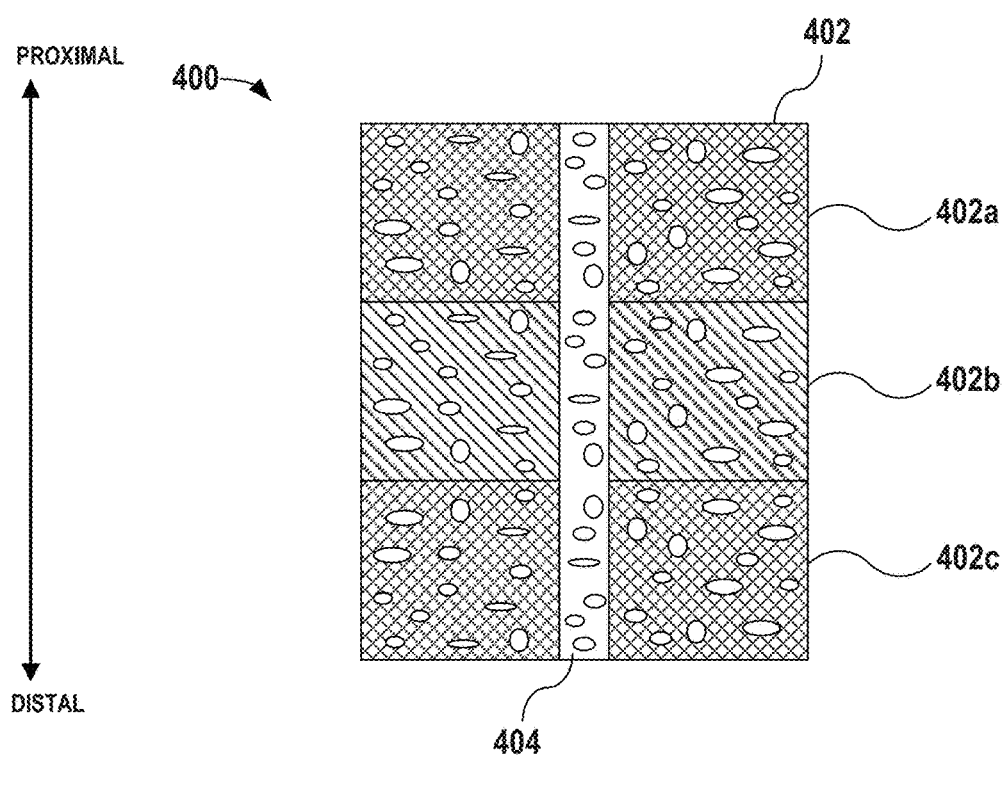
FIGS. 4 and 5 are elevation section views of two additional example instrument guides in accordance with examples of this disclosure.
Figure 5:
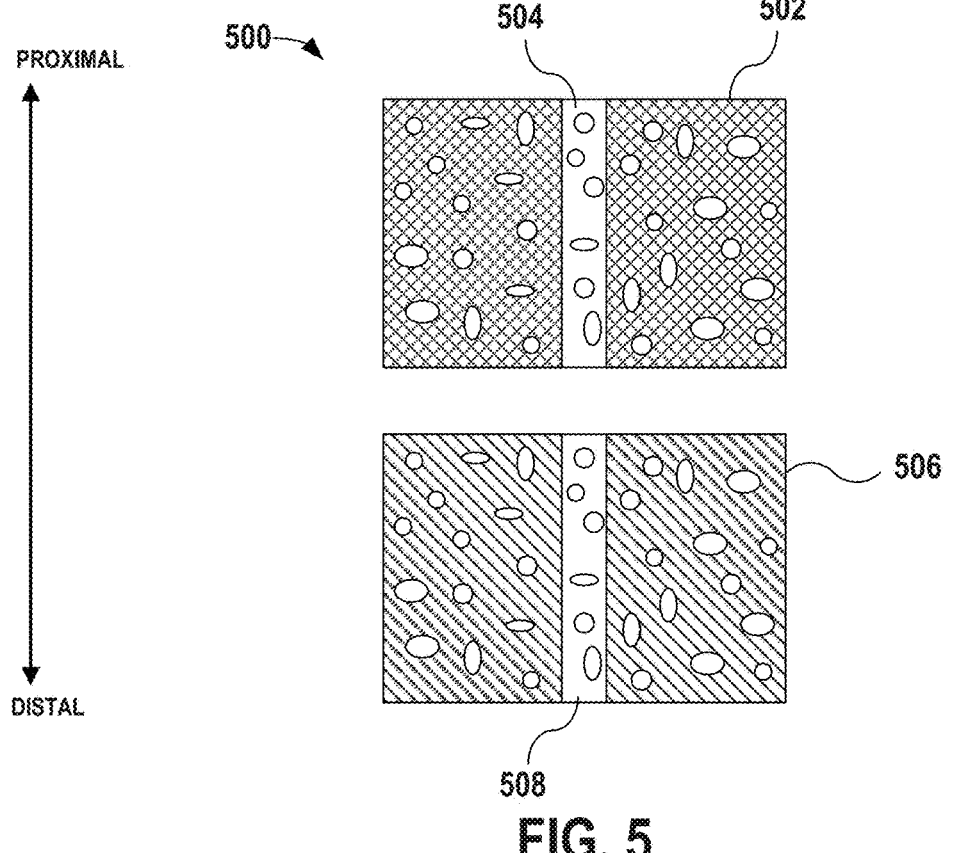

FIGS. 4 and 5 are elevation section views of two additional example instrument guides 400 and 500 in accordance with examples of this disclosure. Medical instrument guides in accordance with this disclosure are shaped, sized, composed of materials, and configured to guide the shaft of a medical instrument as it is inserted into the body of a patient, to lubricate the shaft to reduce friction on the shaft, to optionally seal against the outer surface of the shaft, and to optionally disinfect the shaft of the instrument. Example guides 400 and 500 are two different examples that are configured to lubricate and to disinfect the shaft of a medical instrument guided into the body of a patient by the guides.

In FIG. 4, instrument guide 400 includes guide body 402 and bore 404. Guide body 402 includes first portion 402a, second portion 402b, and third portion 402c. In a similar manner as other example instrument guides described above, guide body 402 of guide 400 is formed from an open cell foam material (e.g., ester- or ether-based polyurethane), and in some examples a different material or open cell configuration (e.g., larger or smaller cells, larger or smaller cell density) may optionally be used for an individual one or each of the different portions 402a, 402b, 402c. Portions 402a, 402b, 402c as shown are arranged in a layered sequence and are in contact with one another. Each of the portions 402a, 402b, 402c may have an optional non-porous skin surface configuration as described above. The thicknesses of the individual portions 402a, 402b, 402c may be varied depending on the type and amount of disinfectant or lubricant to be applied. In the example of FIG. 4, first portion 402a of guide body 402 and third portion 402c of guide body 402 each hold a lubricant, and second portion 402b of guide body 402 holds a disinfectant. The order of application of lubricant and disinfectant may vary during instrument shaft insertion. For example, a disinfectant may be applied first followed by application of a lubricant, or vice-versa. Optionally, two different types of disinfectant or lubricant may be applied. The example shown in FIG. 4 is illustrative of multiple foam portions (e.g., 2, 3, 4, or more) included in an instrument guide body. Other multi-portion combinations (e.g., two or four layered portions) with different instrument shaft additives are possible in example instrument guides in accordance with this disclosure.

In FIG. 5, instrument guide 500 includes first guide body 502 and second guide body 506. First bore 504 extends through first guide body 502, and second bore 508 extends through second guide body 506. First guide body 502 and second guide body 506 of guide 500 are each formed from an open cell foam material as described above. First guide body 502 and second guide body 506 as shown are spaced apart from one another. Each guide body 502, 506 may optionally be a single- or multi-layer foam arrangement as described above, and each (or the individual layers of each) may optionally include a non-porous skin surface configuration as described above. The example shown in FIG. 5 is illustrative of multiple spaced-apart guide bodies (e.g., 2, 3, 4, or more) included in a single instrument guide.

In an example, first guide body 502 and second guide body 506 are formed of the same open cell polymer foam material type, while in other examples first guide body 502 and second guide body 506 are formed of different open cell polymer foam material types. In the case of example instrument guide 500, first guide body 502 holds a disinfectant, and second guide body 506 holds a lubricant so that the instrument shaft is first disinfected and then lubricated with a sterile lubricant as the instrument shaft is inserted through instrument guide 500 and into the patient. In an alternate optional configuration, the order of application of disinfectant and lubricant is reversed.

Figure 6A:
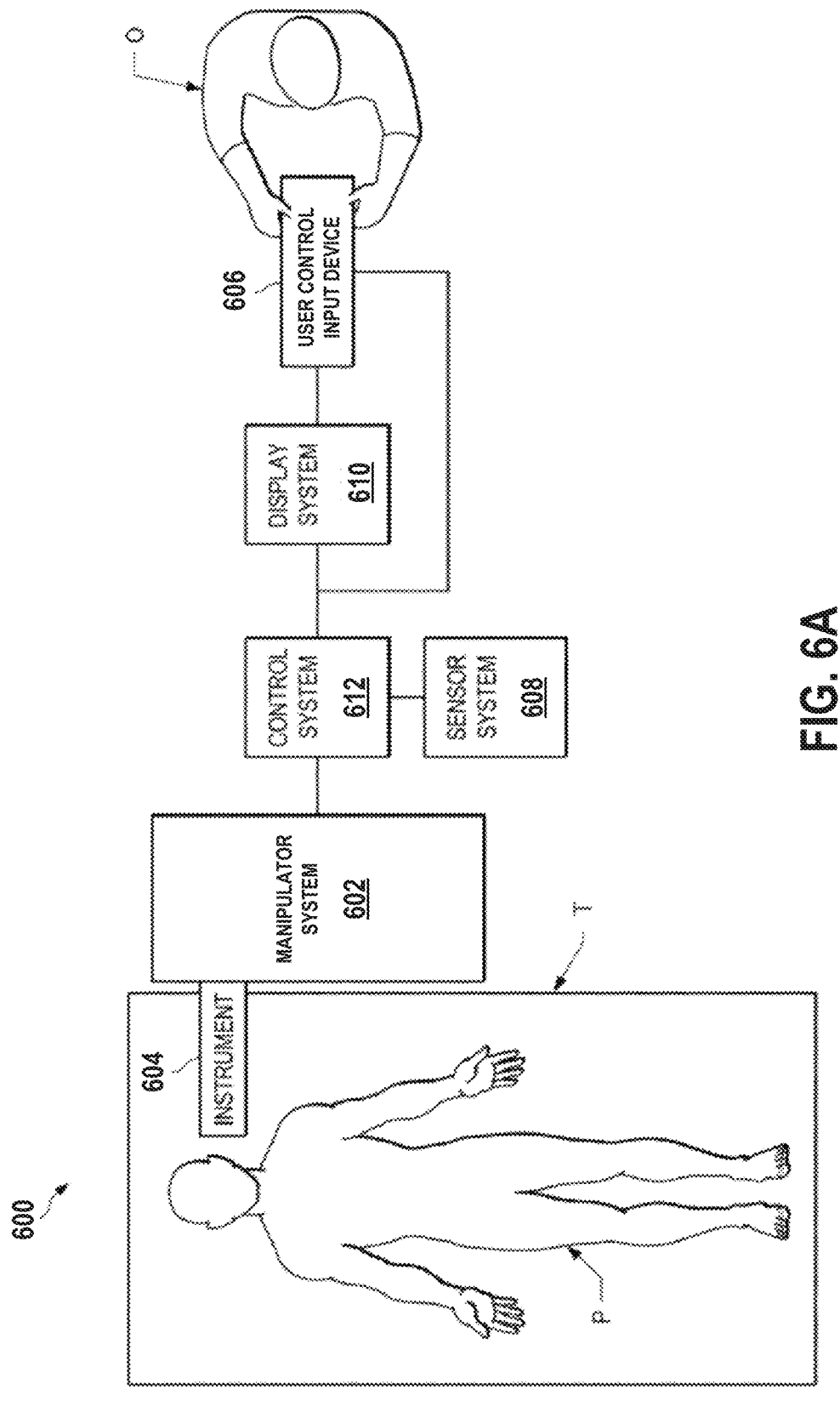
FIGS. 6A-6C depict different aspects of an example teleoperated medical system in which example medical instrument guides in accordance with this disclosure can be employed.
Figure 6B:
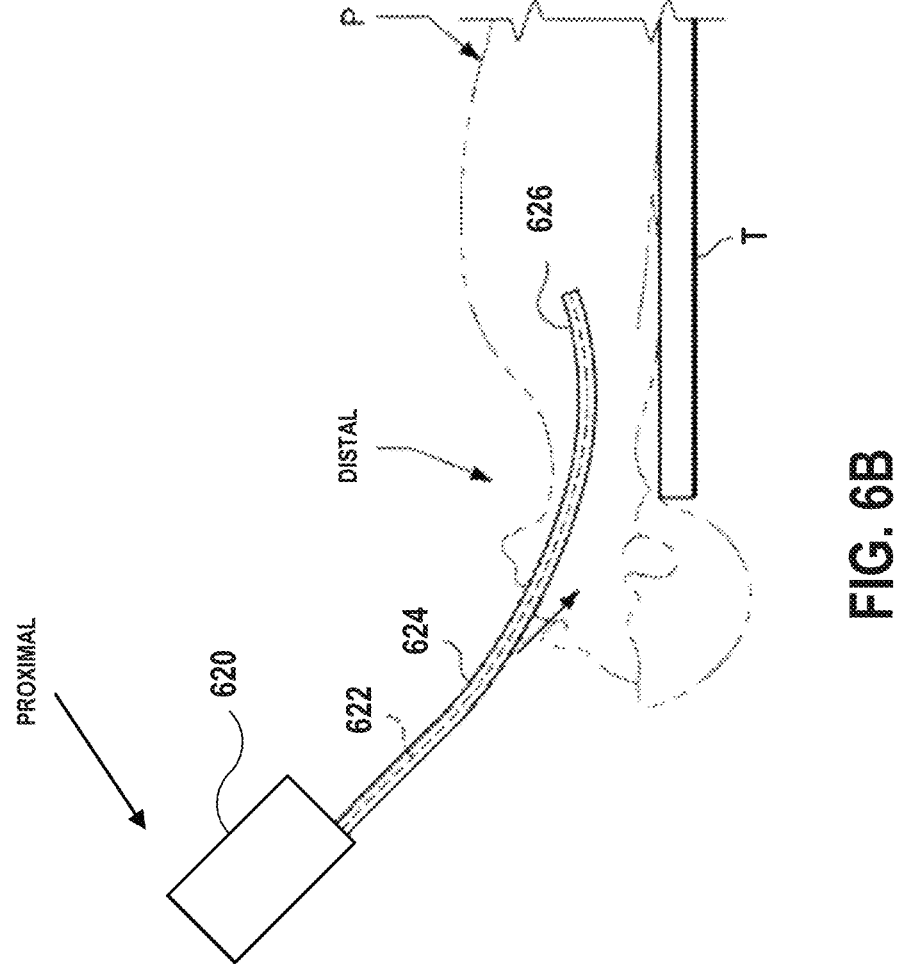
Figure 6C:
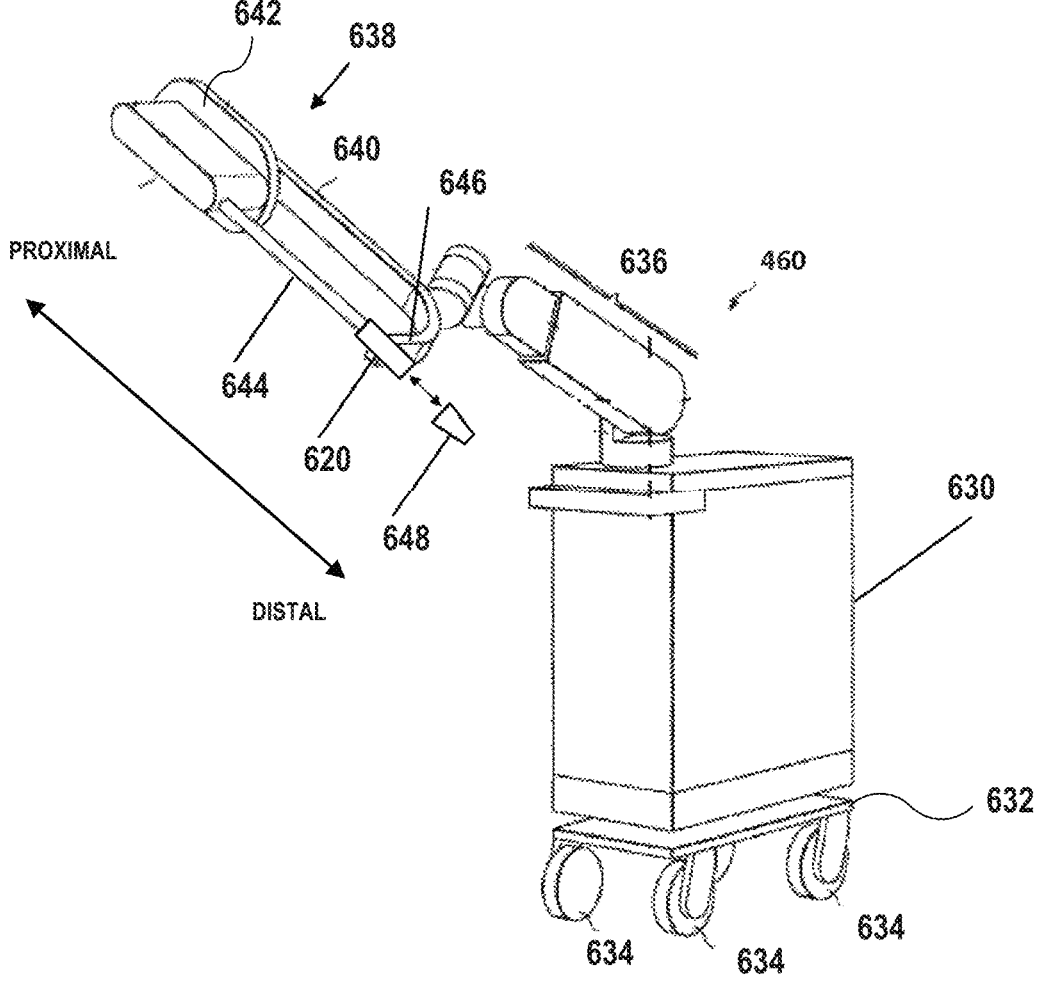

FIGS. 6A-6C depict different aspects of an example medical system 600 in which example medical instrument guides in accordance with this disclosure can be employed. FIG. 6A schematically depicts teleoperated medical system 600, which as shown in FIG. 6C may optionally be a telesurgical system, such as the Ion® Endoluminal System. Medical system 600 illustrates various medical systems suitable for use in diagnostic (e.g., imaging, biopsy) or therapeutic (e.g., excision, repair) procedures, and in related training. The systems, instruments, devices, and methods described herein may be used in relation to human or animal anatomy, cadavers, and animal carcasses.

As shown in FIG. 6A, medical system 600 generally includes a manipulating system 602 for operating a medical instrument 604 in performing various procedures on a patient P. The manipulating system 602 is teleoperated and has one or more motorized and teleoperated or non-motorized mechanical degrees of freedom of motion. Manipulating system 602 is mounted to or near an operating table T. A master user control input device 606 allows an operator O to control instrument 604 via manipulating system 602. The operator O may also optionally view the surgical site with an imaging system as described below.

Master user control input device 606 is located at an operator console, which is usually located in the same room as operating table T, such as at the side of a surgical table on which patient P is located. But, it should be understood that operator O may be located in a different room or a completely different building from patient P. Master user control input device 606 generally includes one or more control devices for controlling instrument 604 via manipulating system 602. The user control input device 606 may include one or more of a variety of input devices, such as a joystick, a trackball, a data glove, and a pistol grip with optional finger trigger, as well as other mechanically-grounded or ungrounded hand-operated controllers, voice recognition devices, body motion or presence sensors, and/or the like. To provide operator O a strong sense of directly controlling instrument 604, the control device may be provided with at least the same degrees of freedom as the associated medical instrument 604. In this manner, the control device provides operator O with telepresence. In some examples, however, the control device may have fewer degrees of freedom than the associated medical instrument 604 and yet still provide operator O with telepresence.

The manipulating system 602 supports medical instrument 604 and includes a manipulator for instrument 604 and typically manipulator support structure, which is a kinematic arm that supports the manipulator. The manipulator support structure optionally includes one or more non-motorized links (e.g., one or more links that may be manually positioned and locked in place) and/or one or more motorized links (e.g., one more links that may be positioned in response to control commands so as to position and hold the manipulator at a desired kinematic pose with reference to the patient. The manipulator assembly 602 may optionally include a plurality of actuators or motors that drive inputs on medical instrument 604 in response to commands from control system 612 based on input from operator O at user control input device 606. The actuators are coupled to medical instrument 604, and they translate and rotate medical instrument 604 in one or more degrees of freedom of movement. Additionally, the actuators can be used to actuate one or more instrument 604 components, such as an articulable end effector for grasping tissue, operating a biopsy device, and the like.

Medical system 600 may include a sensor system 608 with one or more sub-systems for receiving information about the instrument 604 driven by manipulation system 602. Such sub-systems may include a position or orientation sensor system (e.g., an electromagnetic (EM) or optical kinematic pose sensor system). Such sub-systems may include a force sensing system that senses reactive force between the instrument and tissue and feeds back information about the sensed force for output to the user as haptic or other human-perceivable information. Such subsystems may further include an imaging system that captures mono- or stereoscopic images captured by an imaging device at the distal end of instrument 604.

Medical system 600 also includes an optional display system 610 for displaying an image or representation of the surgical site and medical instrument 604 generated by sub-systems of sensor system 608, Display system 610 and user control input device 606 may be oriented so operator O can control medical instrument 604 and user control input device 606 with the perception of telepresence.

In some examples, medical instrument 604 may include components of an imaging system that records a concurrent or real-time image of a surgical site and provides the image to the operator or operator O through one or more displays of medical system 600, such as one or more displays of display system 610. The imaging system may be implemented as hardware, firmware, software, or a combination thereof which interact with or are otherwise executed by one or more computer processors, which may include the processors of a control system 612.

Display system 610 may also display an image of the surgical site and medical instruments captured by the visualization system. In some examples, medical system 600 configuration is such that the relative positions of an image capture device of sensor system 608 and instrument 604 are similar to the relative positions of operator O's eyes and user control input device 606. In this manner operator O can manipulate medical instrument 604 and the hand control input device as if viewing the workspace in substantially true presence.

Medical system 600 also includes control system 612. Control system 612 includes at least one memory and at least one computer processor (not shown) for effecting control between medical instrument 604, user control input device 606, sensor system 608, and display system 610. Control system 612 also includes programmed instructions (e.g., a non-transitory machine-readable medium storing the instructions) to implement some or all of the methods described in accordance with aspects disclosed herein. While control system 612 is shown as a single block in the simplified schematic of FIG. 6A, the system may include two or more data processing circuits with one portion of the processing optionally being performed on or adjacent to manipulation system 602, another portion of the processing being performed at user control input device 606, and/or the like.

The processors of control system 612 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the robotic medical systems described herein. In one example, control system 612 supports wireless communication protocols such as Bluetooth, IrDA, HomeRF, IEEE 802.11, DECT, and Wireless Telemetry.

In some examples, control system 612 may receive force and/or torque feedback from medical instrument 604 via sensor system 608 as describe above. Responsive to the feedback, control system 612 may transmit signals to master assembly 606.

In some examples, control system 612 receives an input from user control device 606 and correspondingly transmits signals instructing one or more actuators of manipulation unit 602 to move medical instrument 604. As described above, medical instrument 604 may extend through an instrument guide in accordance with this disclosure coupled to manipulation system 602. The instrument guide through which the shaft of instrument 604 is translated is configured to guide, lubricate, disinfect, and/or seal against the instrument shaft.

FIG. 6B diagrammatically depicts patient P on table T and positioned to receive and receiving an example medical instrument 604 from manipulator assembly 602 (FIG. 6A). Only a portion of manipulator assembly 602 is depicted in FIG. 6B, including connection device 620 through which instrument 604 and its instrument shaft 622 extend within endotracheal (ET) tube 624 to place instrument 604's distal end 626 at a surgical site within patient P (e.g., within the lung as shown).

In some procedures, such as the example in FIG. 6B, an airway management device such as ET tube 624 is inserted through the nose or mouth of a patient and placed within the trachea. The airway management device is connected to a ventilator or a breathing machine (not shown) and is used as a conduit to open the airway and to carry air into the patient's lungs. The ventilator provides mechanical ventilation during the medical procedure. In other words, the airway management device facilitates artificial ventilation when a patient is unconscious, sedated, or anesthetized during the medical procedure. Medical instrument 622 may then be inserted through the airway management device (e.g. ET tube 624) into the patient to view the trachea and other bronchial passages, to diagnose lung diseases, and/or to treat diseased tissue.

In examples, connection device 620 (e.g., connected to manipulation system 102 of FIG. 6A) includes a medical instrument guide in accordance with examples of this disclosure. As operator O inserts medical instrument 622 (by hand or via a telesurgical system) into patient P through connection device 620, the shaft of instrument 622 is guided by the instrument guide in or connected to connection device 620. The instrument guide through which the shaft of instrument 622 is translated is configured to guide, lubricate, disinfect, and/or seal against the instrument shaft as disclosed herein.

FIG. 6C depicts an example of manipulation unit 602 schematically depicted in FIG. 6A (an Ion® endoluminal system is shown). Manipulation unit 602 includes cart 630 mounted on cart base 632. Optionally, support structure 632, on which cart 630 is mounted, includes wheels 634 to allow positioning of cart 630 at a desired location relative to the operating table T and the patient P. Cart 630 may also house various components including processors, monitors, vacuum equipment, air canisters, cables, etc. for performing various procedures on the patient P.

Connected to the top of cart 630 is support structure 636. Manipulator 638 is coupled to and supported by support structure 636. Manipulator 638 includes insertion stage 640 and a carriage 642 to which an elongate minimally invasive medical instrument 644 is coupled. Movable connection device 620 is coupled to docking spar 646 at a distal end of insertion stage 640. Movable connection device 620 couples medical instrument 644 to endotracheal tube 648, which is schematically represented in FIG. 6C. Instrument 644 can be, for example, a medical instrument including a flexible, elongate shaft.

ET tube 648 is inserted into the mouth and trachea of the patient to help provide mechanical ventilation for the patient and to provide a conduit for elongate device 644 to be inserted into a lung of the patient. While elongate device 644 is being navigated into the lung to facilitate imaging, biopsy, and/or treatment, the patient may experience coughing, unexpected motion, or reduced sedation, which may dislodge the endotracheal tube from the patient and disrupt ventilation, To minimize any consequences of this unexpected motion, movable connection device 620 can be releasable from docking spar 646.

In an example, connection device 620 of FIGS. 6B and 6C can be substantially similar to and/or include portions substantially similar to example connection device 200 described in detail above with reference to FIG. 2. Thus, connection device 620 can function similar to, be similarly constituted with instrument guide 100 in accordance with examples of this disclosure, and can be releasably coupled to docking spar 646 in a similar fashion as connection device 200 (FIG. 2) is described as magnetically releasably coupled to a mounting bracket of a manipulator assembly.

In examples according to this disclosure, including the examples of FIGS. 1-6C, the shaft of a medical instrument that moves through an instrument guide in accordance with this disclosure can be configured to improve the lubrication and/or disinfectant functions of the instrument guide. For example, the medical instrument shaft can include a surface finish that is configured to increase the amount of lubricant deposited on the shaft by the guide and/or modulate the amount in some other manner. In an example, a medical instrument shaft includes a surface finish including either or both of an array of protrusions, e.g. bumps, and an array of depressions, e.g. dimples, recesses, channels, etcetera. Such surface variations, whether protruding from the shaft surface or extending into the shaft surface, can have a variety of distributions per unit surface area and can have a variety of shapes and sizes, including curvilinear and rectilinear protrusions and/or depressions.

Persons of skill in the art will understand that any of the features described above may be combined with any of the other example features, as long as the features are not mutually exclusive. All possible combinations of features are contemplated, depending on clinical or other design requirements. In addition, if manipulating system units are combined into a single system (e.g., a telesurgical system), each individual unit may have the same configuration of features, or one patient-side unit may have one configuration of features and another patient-side unit may have a second, different configuration of features.

The examples (e.g., methods, systems, or devices) described herein may be applicable to surgical procedures, non-surgical medical procedures, diagnostic procedures, cosmetic procedures, and non-medical procedures or applications. The examples may be applicable for training or for obtaining diagnostic information, such as imaging procedures. The examples may be applicable to handling tissue that has been removed from human or animal anatomies and will not be returned to a human or animal, or for use with cadavers or animal carcasses. The examples may be used for industrial applications, general robotic technology uses, manipulation of non-tissue work pieces, as part of an artificial intelligence system, or in a transportation system.

The above detailed description includes references to the accompanying drawings, which form a part of the detailed description. The drawings show, by way of illustration, specific examples in which the invention may be practiced. These examples are also referred to herein as "examples." Such examples may include elements in addition to those shown or described. But, the present inventors also contemplate examples in which only those elements shown or described are provided. Moreover, the present inventors also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first", "second," and "third", etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. Coordinate systems or reference frames are provided for aiding explanation, and implantations may use other reference frames or coordinate systems other than those described herein.

The above description is intended to be illustrative, and not restrictive. For example, the above-described examples (or one or more aspects thereof) may be used in combination with each other. Other examples may be used, such as by one of ordinary skill in the art upon reviewing the above description. The Abstract is provided to comply with 37 C.F.R. § 1.72(b) and PCT Rule 8.1 to allow the reader to quickly ascertain the nature of the technical disclosure. It is submitted with the understanding that it will not be used to limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples, with each claim standing on its own as a separate example or class of examples, and it is contemplated that such examples may be combined with each other in various combinations or permutations. The scope of the invention should be determined with reference to the appended claims, along with the full scope of equivalents to which such claims are entitled.

The claimed invention is:

1. A medical device comprising:
a medical instrument guide;
wherein the medical instrument guide includes a guide body;
wherein the guide body includes a foam and a bore through the foam;
wherein the foam includes a plurality of open cells;
wherein the plurality of open cells holds a biocompatible lubricant; and
wherein the bore is sized to receive a medical instrument shaft and is defined at least in part by a surface exposing the plurality of open cells holding the biocompatible lubricant to the medical instrument shaft; wherein: the foam includes a second plurality of open cells: the second plurality of open cells holds a disinfectant, and the bore is defined at least in part by a second surface exposing the second plurality of open cells holding the disinfectant to the medical instrument shaft.

2. The medical device of claim 1, wherein:
the bore is non-cylindrical.

3. The medical device of claim 1, wherein:
the guide body includes a non-porous skin enclosing at least a portion of the plurality of open cells holding the biocompatible lubricant.

4. The medical device of claim 1, wherein:
the guide body includes an outer proximal surface, an outer distal surface, and an outer side surface extending between the proximal and distal surfaces; and
the outer proximal surface, the outer distal surface, and the outer side surface of the guide body together are a non-porous skin enclosing the open cells holding the biocompatible lubricant.

5. The medical device of claim 4, wherein:
the guide body includes an outer surface; and
the outer surface of the guide body includes a non-porous skin that encloses the open cells holding the biocompatible lubricant.

6. The medical device of claim 1, wherein:
the guide body includes an outer surface; and
the open cells holding the biocompatible lubricant are exposed at the outer surface of the guide body.

7. The medical device of claim 1, wherein:
the guide body includes an end surface;
the bore includes a lead-in surface between the end surface and the surface defining the bore; and
at least a portion of the plurality open cells holding the biocompatible lubricant are exposed at the lead-in surface.

8. The medical device of claim 7, wherein:
the end surface of the guide body includes a non-porous skin enclosing the open cells holding the biocompatible lubricant.

9. The medical device of claim 7, wherein:
the lead-in surface is oriented to receive the medical instrument shaft as the medical instrument shaft is inserted into a patient.

10. The medical device of claim 7, wherein:
the lead-in surface includes a developable surface.

11. The medical device of claim 7, wherein:
the lead-in surface includes a non-developable surface.

12. The medical device of claim 7, wherein:
the lead-in surface includes two smooth surfaces joined at a discontinuity.

13. The medical device of claim 7, wherein:
the end surface is an first end surface;
the guide body includes a second end surface positioned reverse of the first end surface end;
the bore includes a second lead-in surface between the second surface and the surface defining the bore; and
at least a second portion of the plurality open cells holding the biocompatible lubricant are exposed at the second lead-in surface.

14. The medical device of claim 1, wherein:
the bore is dimensioned to include a diameter less than an outer diameter of the instrument shaft.

15. The medical device of claim 1, wherein:
the plurality of open cells holds a disinfectant.

16. The medical device of claim 1, wherein:
the lubricant includes at least one of a grease, oil, or water-based lubricant.

17. The medical device of claim 1, wherein:
the lubricant includes a water-soluble lubricating jelly.

18. A medical system comprising:
a teleoperated medical instrument including a shaft; and
means for guiding the shaft of the medical instrument as the medical instrument is inserted into and retracted from a body cavity of a patient;
wherein the means for guiding includes means for lubricating the shaft of the medical instrument as the shaft moves through the means for guiding, and
wherein the means for lubricating includes a foam with a plurality of open cells that holds a biocompatible lubricant and a bore through the foam that is sized to receive the shaft of the medical instrument and is defined at least in part by a surface exposing the plurality of open cells holding the biocompatible lubricant to the shaft of the medical instrument, and
wherein the foam includes a second plurality of open cells, the second plurality of open cells holding a disinfectant, and the bore being defined at least in part by a second surface exposing the second plurality of open cells holding the disinfectant to the medical instrument shaft.

* * * * *